(12) United States Patent
Irwin et al.

(10) Patent No.: US 9,895,463 B2
(45) Date of Patent: *Feb. 20, 2018

(54) SOLID STATE FRAGRANCING

(71) Applicant: Impact Products, LLC, Toledo, OH (US)

(72) Inventors: John T. Irwin, Sylvania, OH (US); Stephen A. Dukes, North Baltimore, OH (US); Robert James Hayes, Westerville, OH (US); Donald James Staufenberg, Dublin, OH (US); Jeffrey C. Gayer, Sylvania, OH (US)

(73) Assignee: IMPACT PRODUCTS, LLC, Toledo, OH (US)

( * ) Notice: Subject to any disclaimer, the term of this patent is extended or adjusted under 35 U.S.C. 154(b) by 117 days.

This patent is subject to a terminal disclaimer.

(21) Appl. No.: 14/971,013

(22) Filed: Dec. 16, 2015

(65) Prior Publication Data

US 2016/0101205 A1    Apr. 14, 2016

Related U.S. Application Data

(63) Continuation of application No. 14/053,729, filed on Oct. 15, 2013, now Pat. No. 9,278,152, which is a continuation-in-part of application No. 13/803,327, filed on Mar. 14, 2013, now Pat. No. 9,422,697.

(60) Provisional application No. 61/700,926, filed on Sep. 14, 2012.

(51) Int. Cl.
| | |
|---|---|
| *E03D 9/02* | (2006.01) |
| *A61L 9/04* | (2006.01) |
| *A61L 9/12* | (2006.01) |
| *A61L 9/05* | (2006.01) |

(52) U.S. Cl.
CPC ............... *A61L 9/042* (2013.01); *A61L 9/05* (2013.01); *A61L 9/12* (2013.01); *A61L 2209/15* (2013.01)

(58) Field of Classification Search
CPC .................................................. E03D 13/005
USPC ................... 4/222–233; 239/60; 264/177.1
See application file for complete search history.

(56) References Cited

U.S. PATENT DOCUMENTS

| | | | |
|---|---|---|---|
| 4,459,710 A | 7/1984 | Keyes et al. |
| 4,480,341 A | 11/1984 | Richards |
| 4,480,342 A | 11/1984 | Jones |
| 4,530,118 A | 7/1985 | Richards |
| 6,055,679 A | 5/2000 | Goelz et al. |

(Continued)

OTHER PUBLICATIONS www.freshsticks.com, website, Oct. 18, 2013.

*Primary Examiner* — Lori Baker
(74) *Attorney, Agent, or Firm* — James D. Miller; Shumaker, Loop & Kendrick, LLP

(57) ABSTRACT

Fragrance control is provided by articles of manufacture including various solid state fragrancing objects, methods of using such objects, and systems that employ one or more such objects. The solid state fragrancing object can be used to inconspicuously provide fragrance to a user in an environment by disposing the solid state fragrancing object in the environment and configuring the solid state fragrancing object as at least a portion of a fixture within the environment. The fragrancing object can be easy to manufacture, long lasting, provide fragrance that is consistently released over time, provide an indication to the user that the object needs to be replaced, and can hold a desired ratio of fragrance.

26 Claims, 6 Drawing Sheets

(56) References Cited

U.S. PATENT DOCUMENTS

| | | |
|---|---|---|
| 7,093,773 B2 | 8/2006 | Kuiper |
| 8,007,707 B1 | 8/2011 | Brown et al. |
| 2004/0253285 A1 | 12/2004 | O'Leary et al. |
| 2008/0070025 A1 | 3/2008 | Pavlin |
| 2008/0092282 A1 | 4/2008 | Altmann et al. |
| 2008/0241091 A1 | 10/2008 | McGee et al. |
| 2009/0004234 A1 | 1/2009 | Kessler et al. |
| 2009/0158512 A1 | 6/2009 | Stickler et al. |
| 2010/0233146 A1* | 9/2010 | McDaniel ............ A01N 63/02 424/94.2 |
| 2011/0296597 A1 | 12/2011 | Brown et al. |

* cited by examiner

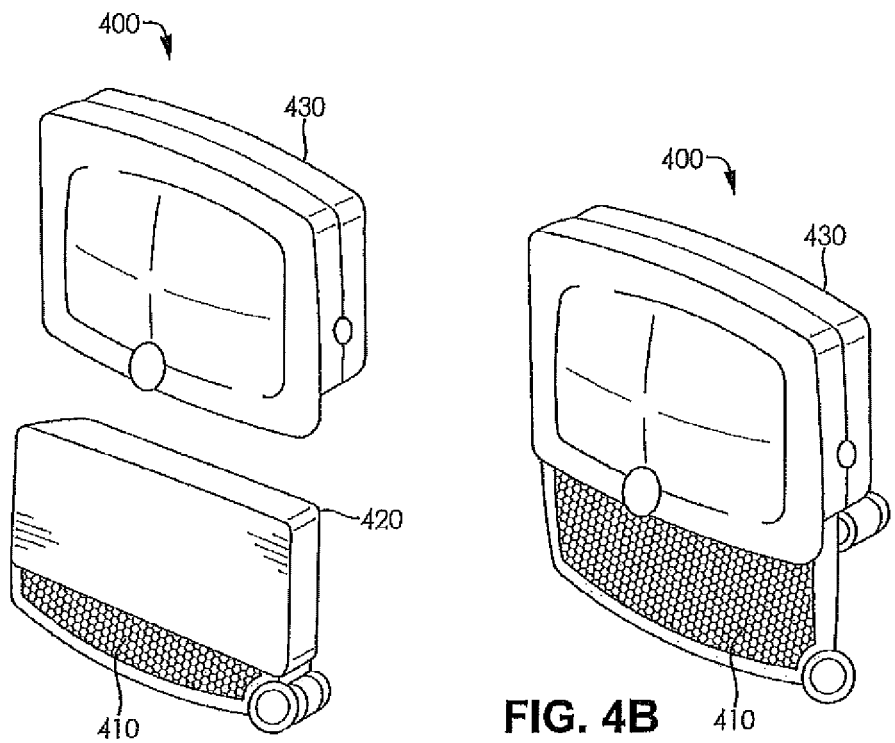
FIG. 4A
FIG. 4B
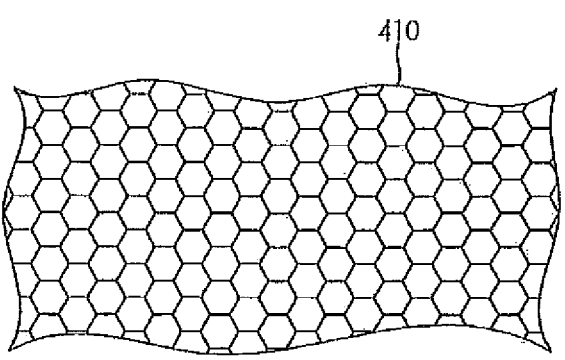
FIG. 4C

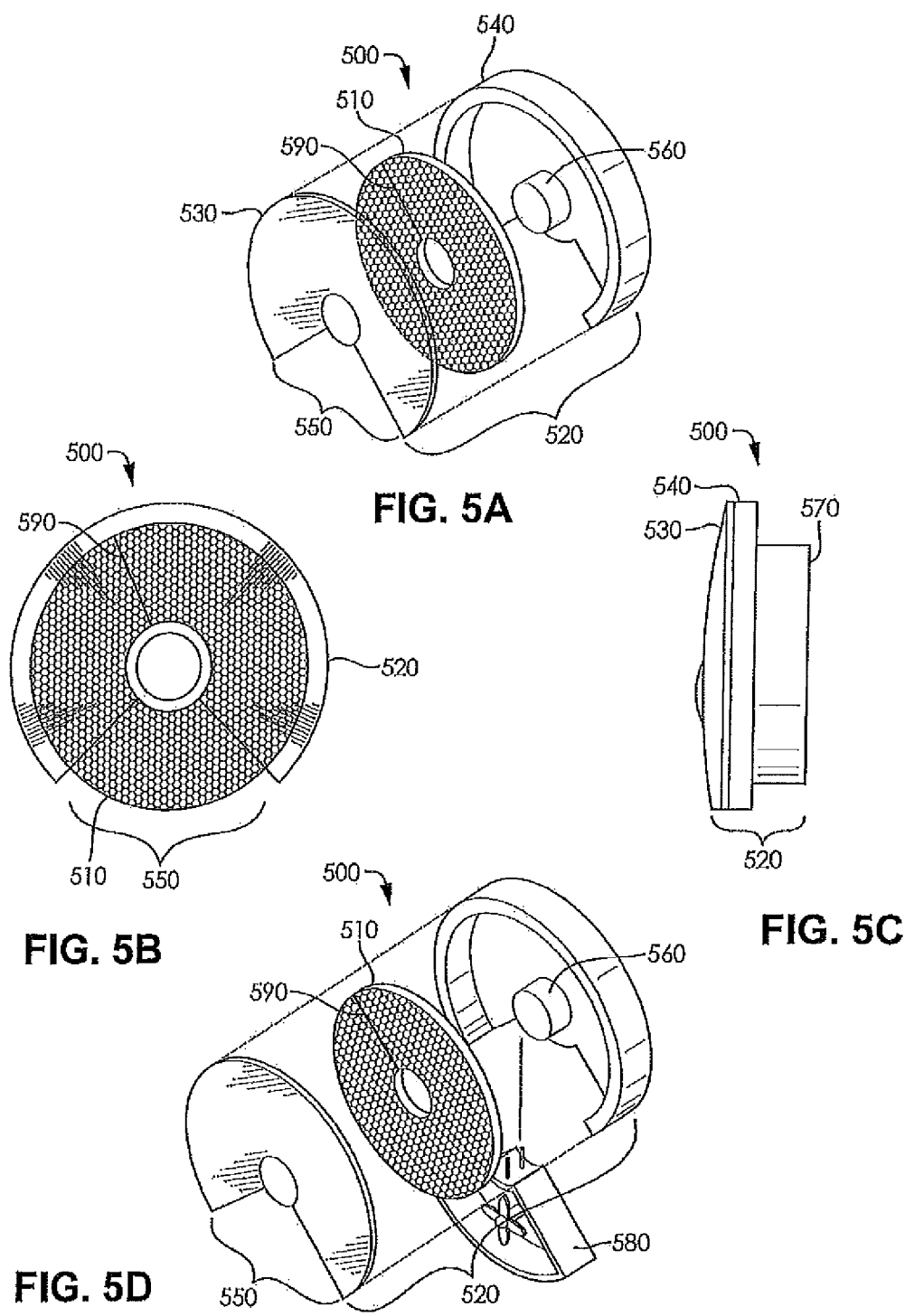

US 9,895,463 B2

SOLID STATE FRAGRANCING

CROSS-REFERENCE TO RELATED APPLICATIONS

This application is a continuation of U.S. application Ser. No. 14/053,729 filed Oct. 15, 2013, which is a continuation-in-part of U.S. application Ser. No. 13/803,327 filed Mar. 14, 2013, which claims the benefit of U.S. Provisional Patent Application Ser. No. 61/700,926, filed on Sep. 14, 2012. The entire disclosures of the above applications are incorporated herein by reference.

FIELD

The present technology relates to articles of manufacture, systems, and processes for fragrance control of one or more various environments. In particular, fragrance control can be employed in an environment, such as a lavatory environment, in order to provide a pleasant fragrance and/or to neutralize or reduce the impact of one or more unpleasant odors.

INTRODUCTION

This section provides background information related to the present disclosure which is not necessarily prior art.

It is often desirable to control the fragrance of certain environments, either to provide a particular fragrance as part of a particular experience or brand identity, for example, or to neutralize or reduce the impact of an unpleasant odor that may be encountered in the particular environment. Both residential and commercial spaces can often benefit from some type of fragrance control. As one example, fragrance control within a lavatory can provide a user with a more pleasant experience and can complement other aspects and perceptions of the environment, such as general cleanliness.

Various fragrancing objects are commonly used to mask or eliminate undesirable odors and emit a preferable scent. Many types of fragrancing objects are available, including those having liquid fragrances or fragrance oils, or plastic objects coated in a fragrance. Fragrancing objects may operate in various ways, including plug-in or spray mechanisms, and may emit or evaporate a fragrance over time. As a non-limiting example, U.S. Patent Application Publication No. 2011/0296597 to Brown et al. discloses an air freshening article that includes a body that is formed from a fragranced plastic. The entire disclosure of the above-mentioned patent application is hereby incorporated by reference.

Some ways of providing environmental fragrance control exhibit various shortcomings. For example, some fragrancing objects are not capable of holding a desired amount or ratio of a fragrancing component, such as a fragrance oil, in comparison to other materials included in the fragrancing object, and may not be easy to manufacture or provide the desired performance. Some fragrancing objects do not provide an optimal release of fragrance over a long period of time and do not provide scent coverage throughout an environment. Conspicuous fragrancing objects can also be subject to theft or vandalism, thereby compromising fragrance control of the environment.

It would be desirable to provide fragrance control including a solid state fragrancing object that is easy to manufacture, long lasting, provides fragrance that is consistently released over time, provides effective scent coverage of an environment, that holds a desired amount or ratio of a fragrant material, and that is less likely to be subject to theft or vandalism.

SUMMARY

The present technology includes articles of manufacture, systems, and methods of inconspicuously providing fragrance to a user in an environment that employ a solid state fragrancing object that is easy to manufacture, provides long lasting fragrance, consistently releases fragrance over time, and holds a desired ratio of fragrance.

In some embodiments, a method of inconspicuously providing fragrance to a user in an environment is provided. The method includes disposing a solid state fragrancing object in the environment where the solid state fragrancing object is configured as at least a portion of a fixture within the environment. The solid state fragrancing object comprises a solid material that includes a fragrancing component.

In certain embodiments, a method of inconspicuously providing fragrance to a user in an environment includes disposing a plurality of solid state fragrancing objects in the environment where each solid state fragrancing object comprises a solid material including a fragrancing component. The solid material comprises a member of the group consisting of a polyether block amide, a polyolefin elastomer, and combinations thereof. The fragrancing component comprises a fragrance oil. Each of the solid state fragrancing objects is configured as at least a portion of at least one fixture within the environment.

In various embodiments, a method of inconspicuously providing fragrance to a user in an environment is provided that includes disposing a solid state fragrancing object in the environment where the solid state fragrancing object configured as at least a portion of a fixture within the environment. The solid state fragrancing object includes a solid material having a fragrancing component. The fixture includes a member selected from the group consisting of a lavatory stall door, a lavatory stall wall, a lavatory stall upright, a urinal divider, a mirror frame, a hand dryer, a paper towel dispenser, a sink counter, a soap dispenser, a shelf, an entry or exit door to the environment, an air vent, a feminine hygiene container, a piece of plumbing, a light fixture, and a waste receptacle. The solid state fragrancing object is removably coupled to the fixture and the solid state fragrancing object is disposed within a line of sight of the user.

In some embodiments, a solid state fragrancing object is provided that comprises a solid material, the solid material including a fragrancing component, wherein the solid material has a substantially constant cross-sectional area in a longitudinal dimension and a surface area to volume ratio of about 0.5:1 to about 50:1. A plurality of solid state fragrancing objects can be used in a system for fragrance control of an environment, where the fragrancing objects are arranged in the environment to provide fragrance substantially throughout the environment.

In certain embodiments, a method of making a solid state fragrancing object is provided. The method includes extruding a material and a fragrancing component to form a solid material, where the solid material includes the fragrancing component. The resulting solid material has a substantially constant cross-sectional area in a longitudinal dimension and a surface area to volume ratio of about 0.5:1 to about 50:1.

In various embodiments, a solid state fragrancing object is provided that includes a solid material, the solid material including a fragrancing component and an aperture configured to couple to a mount, wherein the solid material has a surface area to volume ratio from about 0.5:1 to about 50:1.

In some embodiments, a solid state fragrancing object is provided that comprises a solid material and a dispenser, where the solid material including a fragrancing component. The solid material is slidably disposed within the dispenser and operable to move between an enclosed position and an exposed position. The solid material further includes a surface area to volume ratio from about 0.5:1 to about 50:1.

In certain embodiments, a solid state fragrancing object is provided that includes a solid material and an enclosure enclosing the solid material. The solid material includes a fragrancing component and the enclosure includes an aperture configured to expose a portion of the solid material. The solid material has a surface area to volume ratio from about 0.5:1 to about 50:1.

In various embodiments, a solid state fragrancing object is provided that includes an extruded solid material. The extruded solid material includes a polyether block amide, a polyolefin elastomer, a fragrancing component, and has a plurality of apertures. The solid material is configured as a urinal screen that is sized and shaped to cover at least a portion of a urinal drain.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4A depicts a fourth embodiment of a solid material positioned within a dispenser in an enclosed position along with a mount for receiving the dispenser of a solid state fragrancing object.

FIG. 4B shows the dispenser of FIG. 4A received by the mount where the solid material is in an exposed position.

FIG. 4C shows the solid material of FIG. 4A configured as a honeycomb shaped screen.

FIG. 5A depicts a fifth embodiment showing an exploded view of a solid material placed within an enclosure having an aperture of a solid state fragrancing object.

FIG. 5B is a front view of the solid material and the enclosure of FIG. 5A.

FIG. 5C is a side view of the solid material and the enclosure of FIG. 5A

FIG. 5D is another exploded view of the solid material and the enclosure of FIG. 5A that further includes a fan.

DETAILED DESCRIPTION

Figure 1A:
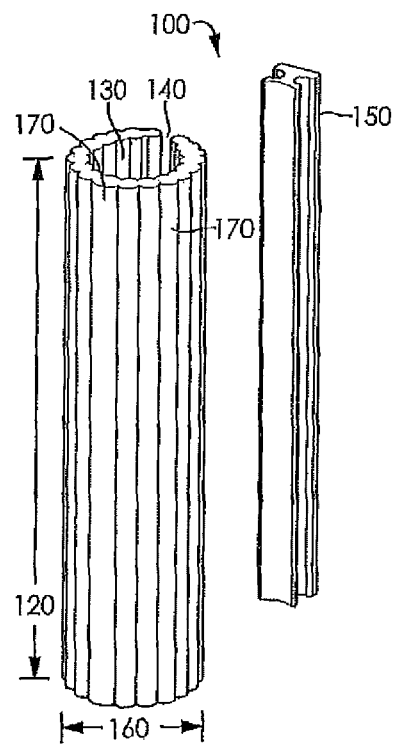
FIG. 1A depicts a first embodiment of a solid material and a mount of a solid state fragrancing object.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except in the examples, or where otherwise expressly indicated, all numerical quantities in this description indicating amounts of material or conditions of reaction and/or use are to be understood as modified by the word "about" in describing the broadest scope of the technology. With respect to any apparent conflict or discrepancy between the present disclosure and documents incorporated herein by reference, the present disclosure controls.

The present technology relates to articles of manufacture including various solid state fragrancing objects, systems that employ such solid state fragrancing objects, and methods of using and making such solid state fragrancing objects. The solid state fragrancing object is easy to manufacture, long lasting, provides fragrance that is consistently released over time, and holds a desired amount of fragrance. In particular, the fragrancing object includes one or more fragrance components that are released or volatilized over time to provide an environment with a desired fragrance.

In some embodiments, the solid state fragrancing object comprises a solid material where the solid material includes the fragrancing component. The solid material can have a substantially constant cross-sectional area in a longitudinal dimension. For example, the longitudinal dimension of the solid material can represent a length where a transverse dimension substantially perpendicular to the longitudinal dimension can represent a height or a width of the solid material. In certain embodiments, the substantially constant cross-sectional area can relate to the shape of an extruder die or head used to form the solid material. The solid material can have a surface area to volume ratio from about 0.5:1 to about 50:1. The surface area to volume ratio is the amount of surface area per unit volume of the solid material, where the surface area is the amount of surface area exposed to air. The ratios provided herein are denoted as surface area: volume, but can also be written as (surface area)/(volume) or as a numerical value having units of inverse distance, where the distance (d) can be meters, inches, etc. I.e., about 0.5:1 to about 50:1 can be written as about 0.5 $d^{-1}$ to about 50 $d^{-1}$.

In various embodiments, the solid state fragrancing object can be configured to have a certain surface area to volume ratio and can also be configured to have a certain surface area to environment volume ratio. As one example, the solid state fragrancing object can provide a particular surface area to volume ratio, where the ratio is tailored to particular applications. In some cases, the solid state fragrancing object can be configured with a greater surface area for a fixed volume to increase the transmission rate of the fragrance component out of the fragrancing object to the atmosphere; e.g., the solid state fragrancing object can configured as a porous material or screen. In other cases, the solid state fragrancing object can be configured with a reduced surface area for a given volume to reduce the transmission rate of the fragrance component out of the fragrancing object to the atmosphere; e.g., the solid state fragrancing object can be configured as a solid shape, such as a puck or sphere. As another example, the solid state fragrancing object can have a surface area to environment volume ratio to provide a certain transmission rate or amount of the fragrance component per atmosphere volume. In certain cases, a square inch of fragranced surface area to environmental cubic foot volume ratio range can be about 0.01 to about 0.1.

The solid material of the solid state fragrancing object includes the fragrance component, such as a fragrance oil. Fragrance oils, also known as aroma, aromatic, and flavor oils, include single or blended synthetic compounds and/or natural essential oils. The fragrance oil can be diluted with a carrier oil or other solvent, such as various vegetable oils, mineral oil, or propylene glycol. Examples of various fragrance oils include orange, *Mentha arvensis*, peppermint, cedarwood, lemon, *Eucalyptus globulus*, *Litsea cubeba*, clove (leaf), and spearmint. The fragrance component can be loaded into the solid material in various amounts. For example, in some embodiments the solid material can include about 0.01% by weight of the fragrancing component to about 66% by weight of the fragrancing component. In various embodiments, the solid material can include at least about 20% by weight of the fragrancing component and in other embodiments the solid material can include at least about 25% by weight of the fragrancing component.

Various loadings of the fragrancing component can provide for a persistent and perceptible fragrance over a given period of time. For example, in some embodiments the fragrancing component can be perceptible for at least about 30 days within an environment of 800 cubic feet surrounding the solid state fragrancing object, and in other embodiments the fragrancing component can be perceptible for at least about 60 days within an environment of 800 cubic feet surrounding the solid state fragrancing object. By perceptible, it is meant that at least 50% of people on a test panel can detect the odor. For example, the environment containing the solid state fragrancing object and an environment without the solid state fragrancing object (as a reference) are presented to a group of panelists. In comparing the fragrance present in each environment, the panelists are asked to report if they can detect a difference between the environments. The test and perceptions by the panelists can be repeated as necessary to afford statistical relevance.

In addition to the fragrancing component, the solid material can comprise one or more various materials that are substantially solid at room temperature and maintain a substantially solid form when admixed with a fragrancing component, such as a liquid fragrancing oil. In this way, the solid state fragrancing object remains substantially solid and able to retain its shape when deployed within an environment. Suitable materials include various polymeric materials and porous materials that can absorb the fragrancing component to thereby limit or control the rate at which the fragrancing component is emitted from the solid state fragrancing object.

In certain embodiments, the solid material can include a thermoplastic elastomer comprising a polyether block amide (PEBA). The PEBA can be obtained by polycondensation of a carboxylic acid polyamide with an alcohol termination polyether to provide a block copolymer with a sequence of polyamide and polyether segments. The block copolymer includes linear chains of relatively rigid polyamide and relatively soft polyether segments. Absorption and controlled release of volatile molecules (e.g., fragrancing components, fragrancing oils) can occur through the polyether phase of the material. The PEBA generally exhibits a good resistance to chemicals and some solvents. One source of a suitable polyether block amide includes PEBAX™ polyether block amides from Arkema Inc. (King of Prussia, Pa.). The PEBA can provide improved absorption and improved release of the fragrance component in comparison to other materials.

In some embodiments, the solid material can include a polyolefin elastomer (POE). Examples of suitable polyolefin elastomers include polyisobutylene (PIB), ethylene propylene rubber (EPR), ethylene propylene diene monomer (M-class) rubber (EPDM rubber). Other examples include various copolymers of ethylene and another alpha-olefin, such as butene or octene; e.g., copolymers of ethylene-butene or ethylene-octene. POEs can be produced in various ways, including use of a metallocene catalyst, as is known in the art. Various POEs can be produced using monomer components of propylene, ethylene, butene, octene and/or hexene. Two examples of suitable polyolefin elastomers are Polyolefin Elastomer 999 Offgrade (an ethene-1-octene copolymer) and ENGAGE™ 8411 polyolefin elastomer (an ethylene-octene elastomer), both from Dow Chemical Co. (Midland, Mich.).

In various embodiments, the solid material can include both a polyether block amide (PEBA) and a polyolefin elastomer (POE). The PEBA can be combined with the POE in amounts ranging from about 1% by weight PEBA with about 99% by weight POE to about 99% by weight PEBA with about 1% by weight POE. Certain embodiments of the solid material include where the PEBA makes up at least 10% of the solid material, the POE makes up to at least 40% of the solid material, and the fragrancing component makes up to at least 15% of the solid material. In various embodiments, the balance of the solid material can comprise the PEBA, the POE, the fragrance component, and/or an additional material or additive. The additional material or additive can comprise a polymeric material or can be a nonpolymeric material. For example, the solid material can include at least one additive, such as an odor neutralizer, a sequesterant, a counteractant, an enzyme, and a colorant.

The solid state fragrancing object can be formed in various shapes and sizes. The fragrancing object may include one or more separate pieces that are assembled together and/or the fragrancing object may be assembled with other materials or coupled to other components or materials. For example, the fragrancing object can be coupled to a holder or mount that is affixed to a wall, ceiling, floor, or some other fixture within the environment. In some embodiments, the solid state fragrancing object can take the form of a rod, tube, blade, clip-on fragrance tube, slide-in fragrance blade, disk, cartridge, signage, kick plate, ornamental object, maintenance aid such as a moppable floor mat or dispenser mat, air vent or portion of an air vent, screen, a drain screen, urinal screen, or various air freshener shapes.

The solid state fragrancing object can also have an adhesive on a portion of the solid material, where the adhesive is operable to couple the solid state fragrancing object to a surface. For example, the solid state fragrancing object can be in the form of a sheet, strip, panel, signage, or decal with adhesive on one side. The adhesive can be in the form of an adhesive backing that allows for peal-and-stick applications of the fragrancing device. The solid state fragrancing object can take the form of signage or display a logo, and can be formed in different sizes. The solid state fragrancing object can be located throughout an environment, where it can be affixed to fixtures, walls, and various objects, including waste receptacles, change tables, urinal mats, stalls, etc. Presence of the fragrancing object can provide fragrancing control within the environment.

In certain instances, it may be desirable to inconspicuously provide fragrance within an environment. Placing one or more fragrancing objects in an environment can interfere with the aesthetics or decor, especially where the fragrancing object is recognizable as such. Readily identifiable fragrancing objects may also be moved about the environment by a user and placed in a location that is less optimal for fragrance control. The user may try to hide the fragrancing object, for instance, or may relocate it to free up needed space or to redistribute fragrance for odor control in another portion of the environment. Likewise, maintenance or custodial persons may relocate the fragrancing object when performing maintenance or cleaning. Such movement of the fragrancing object may interfere with optimal fragrance coverage throughout the environment, providing over-fragranced areas and under-fragranced areas. Identifiable fragrancing objects may also be the target of theft or vandalism. Inconspicuously providing fragrance within an environment therefore can maintain optimal fragrance coverage by preventing relocation, theft, or vandalism of fragrancing objects.

Accordingly, various methods of inconspicuously providing fragrance to a user in an environment are provided herein. In one such method, a solid state fragrancing object is disposed in the environment where the solid state fragrancing object is configured as at least a portion of a fixture within the environment. As described herein, the solid state fragrancing object can comprise a solid material including a fragrancing component and further include the various other aspects as described herein.

The solid state fragrancing object can be disposed within a line of sight of the user and yet remain inconspicuous. For example, as the solid state fragrancing object is configured as at least a portion of a fixture in the environment, the solid state fragrancing object appears as something it is not; i.e., where the solid state fragrancing object is not readily identifiable as a fragrancing object. The user simply sees the solid state fragrancing object as a part or extension of the preexisting fixture. That is, the solid state fragrancing object can be within a line of sight of the user, but is adapted to blend into or appear as if it has another function or purpose. The fragrancing object can be configured as at least a portion of the fixture within the environment, where it can partially cover, completely cover, or extend part of the fixture.

The solid state fragrancing object can also be disposed out of the line of sight of the user. For example, the fragrancing object can be placed on the underside or backside of a fixture that is not typically viewable from a user within the environment. Other locations out of the line of sight of the user of the environment include inside the lid of a container or receptacle, under a sink or counter top, conforming to the shape of plumbing, including pipes and drains, configured as part of heating, ventilation, and air conditioning (HVAC) systems and/or electrical conduit. Again, the fragrancing object can still be configured as at least a portion of the fixture within the environment, where it can partially cover, completely cover, or extend part of the fixture. In this fashion the solid state fragrancing object still appears as something else or part of something else, where a user looking under a sink counter, for example, would not readily identify the solid state fragrancing object as a fragrancing object or other type of air freshener.

One or more solid state fragrancing objects can be configured as at least a portion of one or more various fixtures within the environment. The following non-limiting examples are provided to illustrate how such fragrancing objects can be mounted, used, or installed to provide fragrance coverage. The solid state fragrancing object can be coupled to at least a portion of the fixture where the solid state fragrancing object appears as, covers, or replaces a trim or edging piece of the fixture. In some instances, the solid state fragrancing object can be configured as a portion of a room partition or divider, such as a lavatory toilet stall or urinal divider. For example, the solid state fragrancing object can be positioned and/or formed to appear as trim or edging that runs along a length of a lavatory stall edge. The top, bottom, or vertical edges of the walls of a stall or a door of a stall can serve as locations. Stall uprights connecting the walls of the stall to the floor and/or ceiling are further locations. Likewise, the solid state fragrancing object can be configured as at least a portion of moulding or edging along the walls of the environment, including sites such as the wall-ceiling junction and the wall-floor junction. Other embodiments include where the solid state fragrancing object is disposed on a railing or a column. The solid state fragrancing object can also be used as at least a portion of a mirror, such as the mirror frame, where the solid state fragrancing object is coupled or covers at least a portion of the mirror frame or where the solid state fragrancing object takes the place of a mirror frame. Other lavatory fixtures can have one or more solid state fragrancing objects disposed thereon, including the top, bottom, and/or sides of wall mounted hand dryer, a paper towel dispenser, and a soap dispenser. The solid state fragrancing object can be positioned on a sink counter, appearing as a trim or edging piece, and can be placed on or over plumbing to appear as insulation or part of the pipework itself. Shelving and shelving brackets can have the solid state fragrancing object configured to appear as a portion thereof. An entry/exit door to the environment can be trimmed or framed with one or more solid state fragrancing objects, where the solid state fragrancing object can be further configured to appear as or cover a portion of a panel of the door, including a kick plate, push plate, or handle on the door. Air vents, duct work, or other portions of an HVAC system can have disposed thereon one or more solid state fragrancing objects. For example, the solid state fragrancing object can cover or provide a trim appearance of one or more fins or vanes of an air vent, including where the solid state fragrancing object is directly clipped or snapped thereon. The solid state fragrancing object can also be used on or within a container, including a waste receptacle or feminine hygiene container. The solid state fragrancing object can appear as a trim or lip of the container lid or can even replace a container lid. In certain cases, the solid state fragrancing object can be coupled to a base or mount disposed on the underside of the container lid. Other fixtures include light fixtures, including shades, screens, or covers thereof, whether exposed or recessed.

While many of the preceding examples pertain to a lavatory environment, the present technology can be applied to fixtures in other environments, including residential and commercial environments, including kitchens, dinning areas, bedrooms, living areas, work spaces, athletic facilities, locker rooms, and outdoor environments such as patios. The present technology can also be applied to fixtures in environments including foyers, common areas, automobiles, trucks, buses, trains, recreational vehicles, campers, watercraft, and various motor vehicles. For example, the solid state fragrancing object can be configured as at least a portion of fixtures including tables, chairs, desks, office cubicles, shelving, display cases, etc. Solid state fragrancing objects can be within a line of sight of and/or can be out of the line of sight. The solid state fragrancing object can also be disposed on a fixture that may require a ladder or step stool to access. In this way, the lack of easy access coupled with the inconspicuous appearance of the solid state fragrancing object can further reduce the chance of theft or vandalism.

As illustrated by the preceding examples, the solid state fragrancing object can inconspicuously provide fragrance by covering a preexisting portion of the fixture. However, the solid state fragrancing object can also replace or even form a new portion of the fixture where it appears as an extension of the fixture; e.g., where the solid state fragrancing object is used to frame a glass mirror that previously did not have a frame. The inconspicuous nature of the solid state fragrancing object can also be tailored by substantially matching a color and/or a texture of the fixture. The solid state fragrancing object can also have a substantially muted or neutral color, such as a shade of gray, brown, tan, white, black, etc. in contrast to vibrant shades of red, yellow, orange, blue, green, etc.

In some cases, the solid state fragrancing object can be removably coupled to the fixture, thereby allowing the solid state fragrancing object to be easily replaced with either a solid state fragrancing object having a different fragrance or a new solid state fragrancing object when the solid state fragrancing object no longer emits a desired amount of fragrance. The solid state fragrancing object can also be removed to provide cleaning access or fixture repair, depending on the nature of the fixture to which it is coupled. Convenient means to removably couple the solid state fragrancing object to the fixture include various mounts, bases, adhesives, double-side tape, and various fasteners. Alternatively, the solid state fragrancing object can be configured to be directly coupled to the fixture, e.g., configured to clip or snap onto the fixture, or the solid state fragrancing object can have some type of integral retaining means that allows the solid state fragrancing object to directly fit into, onto, or over at least a portion of the fixture.

More than one solid state fragrancing object can be disposed in the environment on more than one fixture. More than one solid state fragrancing object can also be configured as multiple portions of the same fixture. For example, a plurality of solid state fragrancing objects can be disposed throughout the environment on various fixtures with a portion of the plurality of solid state fragrancing objects configured as portions of the same fixture. Arranging multiple solid state fragrancing objects in this manner can optimize fragrance coverage and scent mapping throughout the environment. Use of multiple solid state fragrancing objects also allows the solid state fragrancing objects disposed on different fixtures, or even the same fixture, to have different fragrancing components. Different fragrances can be mapped to provide a dynamic and changing scent experience as the user moves through the environment. For example, certain areas of the environment can be provided with greater fragrance and/or a different fragrance compared to other areas of the environment.

In some embodiments, the solid state fragrancing object can be designed and formed in various aesthetic shapes, colors, and textures that are within the line of sight within the environment, but appear as at least a portion of the fixture in the environment. Fragrancing objects can therefore be part of the decor, include a decor theme, or can match or provide accents to the decor. The fragrancing objects can also be designed in various shapes, colors, and textures to blend into the environment. Discretely installing the fragrancing objects out of the line of sight can be done to prevent interference with the aesthetics of an environment. However, as the solid state fragrancing object is configured as at least a portion of the fixture, the incidence of vandalism or theft is minimized. Discrete shapes and colors can also be used where the solid state fragrancing object matches or blends in with the environment location to which it is coupled. The solid state fragrancing object can therefore be configured for use in a stealth fashion to minimize conspicuousness by using darker or environment-matching colors and coupling the fragrancing object to preexisting fixtures to make the fragrancing object appear to be part of the preexisting fixture or object, and by using the fragrancing object in place of preexisting objects.

In various embodiments, the present technology provides systems for fragrance control of an environment. A system can include a plurality of solid state fragrancing objects, with each fragrancing object comprising a solid material that includes a fragrancing component. Each solid material can have a substantially constant cross-sectional area in a longitudinal dimension and a surface area to volume ratio of about 0.5:1 to about 50:1. The plurality of fragrancing objects is arranged in the environment to provide fragrance substantially throughout the environment. For example, the system can employ solid state fragrancing objects as described herein. The individual fragrancing objects can each include a fragrancing component that is perceptible for at least about 30 days or at least about 60 days within an environment of 800 cubic feet surrounding the solid state fragrancing object. In this way, the fragrancing objects of the system can be deployed throughout the environment so that perceptible fragrance zones substantially overlap or nearly overlap. The system can therefore minimize space in the environment where the various fragrancing components are not perceptible and can provide a substantially constant fragrance experience as one moves through the environment. The fragrancing components in the various fragrancing objects can be the same or different, such that the system can be tailored to provide a continuous fragrance or different regional fragrances within the environment.

The plurality of fragrancing objects employed in the system can include many forms, including the various fragrancing objects described herein. For example, in certain embodiments at least one of the solid state fragrancing objects can be configured as a sign, configured as a kick plate on a door, coupled to a toilet divider or urinal divider, coupled to a toilet door, coupled to an air vent, or coupled to a pipe. For example, one fragrancing object in the system can be configured as a wall sconce for a lamp in a lavatory, while another fragrancing object is placed alongside the bottom edge of a lavatory stall or urinal divider. Several fragrancing objects can be used together and formed in various shapes, designs, and colors to provide a scent design theme.

Figure 1B:
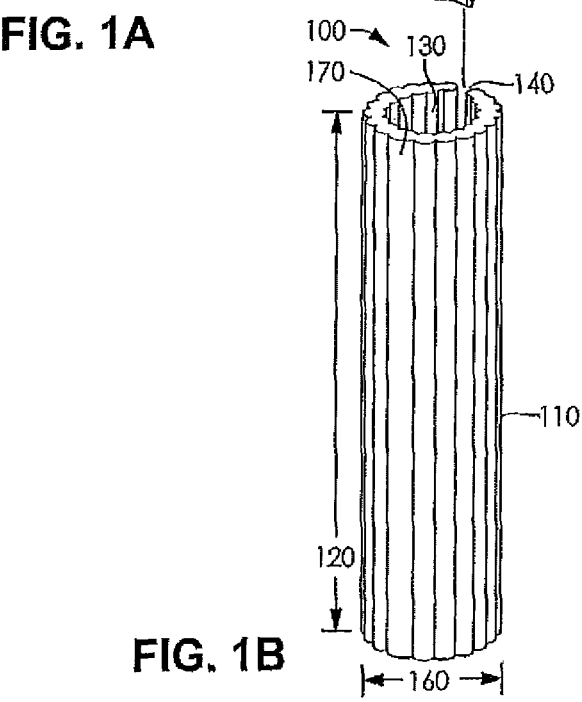
FIG. 1B shows the solid material of FIG. 1A positioned to engage the mount.
Figure 1C:
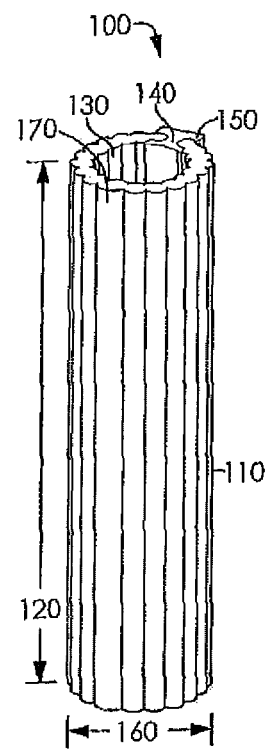
FIG. 1C shows the solid material of FIG. 1A coupled to the mount.

With reference to FIGS. 1A-1C, a first embodiment of a solid state fragrancing object 100 is shown. The fragrancing object 100 includes a solid material 110 that contains the fragrancing component. As can be seen, the solid material 110 has a substantially constant cross-sectional area in a longitudinal dimension 120. The surface area to volume ratio of the solid material 110 lies between about 0.5:1 to about 50:1. An interior portion 130 of the solid material 110 is hollow. The solid material 110 has a recess 140 running in the longitudinal dimension 120 that can be used to couple and receive a mount 150. The mount 150 can be coupled to a wall or other structure in an environment so that the solid material 110 can be easily replaced when the fragrancing component is diminished and no longer adequate. FIG. 1A shows the solid material 110 separated from the mount 150. FIG. 1B shows the solid material 110 positioned to slide the mount 150 into the recess 140. FIG. 1C shows the solid material 110 coupled to the mount 150. The mount 150 allows mounting the solid material 110 such that air can circulate all around and through the solid material 110 so that fragrance is dispensed from the inside and the outside.

As depicted in FIGS. 1A-1C, the solid material 110 has a tube-like shape having a transverse dimension 160 that is less than the longitudinal dimension 120. The solid material 110 is also formed with a plurality of protuberances 170 that run in the longitudinal dimension 120 and increase the surface area of the solid material 110. The protuberances 170 shown are formed as ribs or Quonset but shaped structures; however, the protuberances 170 can be formed in various other shapes and can project radially further from a remainder of the solid material 110 or project radially less from the remainder of the solid material than shown. The solid material 110 depicted in FIGS. 1A-1C also includes protuberances 170 projecting into the hollow interior portion 130. It should be noted that air can flow through the hollow interior portion 130 using the open ends of the solid material 110 and that the hollow interior portion 130 contributes to the overall surface area of the solid material 110.

The solid state fragrancing object, such as the fragrancing object 100 shown in FIGS. 1A-1C, can also be used without the mount 150. In this case, the solid material 110 can be snapped onto or clipped onto a structure directly. For example, the recess 140 can allow the solid material 110 to be slipped over a length of pipe under a sink or snapped/clipped onto an edge or lip of a toilet door or stall, or onto urinal divider, in a lavatory environment.

Figure 2A:
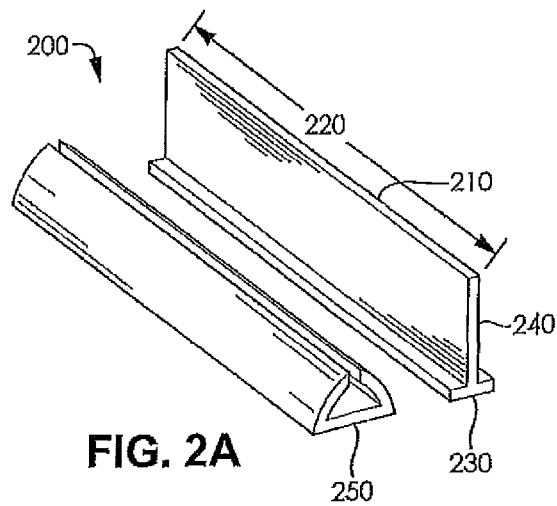
FIG. 2A depicts a second embodiment of a solid material and a mount of a solid state fragrancing object.
Figure 2B:
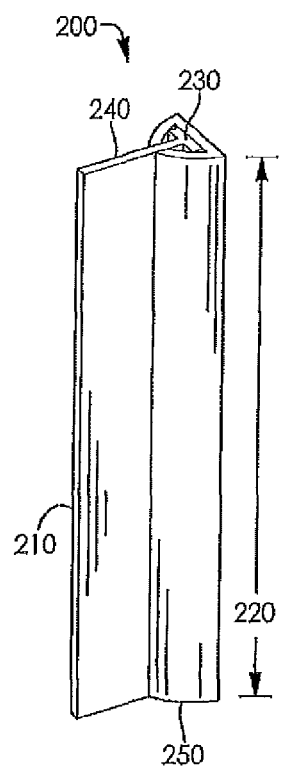
FIG. 2B shows the solid material of FIG. 2A coupled to the mount.
Figure 2C:
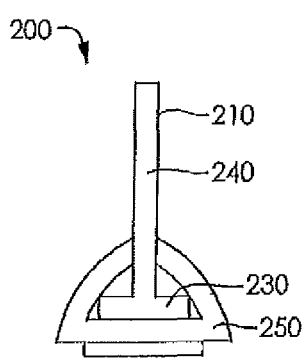
FIG. 2C shows an end view of the solid material of FIG. 2A coupled to the mount.

With reference to FIGS. 2A-2C, a second embodiment of a solid state fragrancing object 200 is shown. The fragrancing object 200 includes a solid material 210 that contains the fragrancing component. The solid material 210 has a substantially constant cross-sectional area in a longitudinal dimension 220. The surface area to volume ratio of the solid material 210 lies between about 0.5:1 to about 50:1. A base 230 forms one portion of the solid material 210 and a blade 240 forms another portion of the solid material 210, where the base 230 and the blade 240 run in the longitudinal dimension 220 and the blade 240 extends laterally outwardly from the base 230. As shown, the blade 240 comprises a greater portion of the solid material 210 than the base 230. In this way, the blade 240 provides a surface area exposed to the environment to release the fragrancing component. However, in other embodiments the blade 240 can comprise an equal or lesser portion of the solid material 210 than the base (not shown). The base 230 couples the solid material 210 to a mount 250 by sliding the base 230 into the mount 250. The mount 250 can be coupled to a wall or other structure in an environment so that the solid material 210 can be easily replaced when the fragrancing component is diminished and no longer adequate. FIG. 2A shows the solid material 210 separated from the mount 250. FIG. 2B shows the solid material 210 coupled to the mount 250, where the base 230 is slid into the mount 250. FIG. 2C shows an end view of the solid material 210 coupled to the mount 250, with the base 230 within the mount 250 and the blade 240 projecting from the mount 250.

In some embodiments, the solid state fragrancing object can be formed by extrusion, where a material and a fragrancing component are extruded to form a solid material, the solid material including the fragrancing component. The extrusion process results in the solid material having a substantially constant cross-sectional area in a longitudinal dimension and a surface area to volume ratio of about 0.5:1 to about 50:1. For example, an extruder with various dies or extruder heads can be employed to provide various cross-sectional shapes to the resulting solid material. The material and the fragrancing component may be in a liquid, semi-liquid, gel, or paste-like phase when present in the extruder, but become necessarily solid following extrusion to form the solid material. In particular, the material and the fragrancing component can be mixed in the extruder followed by extruding the material and the fragrancing component to form the solid material including the fragrancing component. The mixing can include melt-mixing the material and the fragrancing component in the extruder.

Extrusion can allow loading of the fragrancing component into the resulting solid material at levels that cannot be achieved using other means. For example, the extrusion process can provide a solid material that includes between 0.01% to about 66% by weight of the fragrancing component. In some cases, the extrusion process can provide a solid material that includes between about 10% to about 30% by weight of the fragrancing component. Improved loading of the fragrancing component can be furthered by performing the extrusion process between about 160 to about 210 degrees Centigrade. In this way, loss of volatile fragrancing oils used as the fragrancing component can be minimized.

As a further example, the solid state fragrancing object can be formed as follows. A material comprising a polyether block amide and a polyolefin elastomer can be used with a fragrancing component. For example, the polyether block amide and a fragrance oil (as the fragrancing component) can be tumbled together in a drum without the addition of heat. The polyolefin elastomer is then added along with any additives, such as a colorant. The mixture of the material (i.e., the polyether block amide and polyolefin elastomer) and the fragrancing component can then be extruded, as described above.

Alternatively, the material and the fragrancing component can be processed by other means, such as blending, pre-molding, molding, forming, and various post-forming processes. Various molding methods can be used including injection molding, blow molding, rotational molding, and extrusion molding. Alternatively, different parts of the various materials and components can be mixed and molded in a batch process or in a continuous process using an extruder, for example. Examples of post forming processes include die cutting, shaping, trimming, bending, braiding, weaving, of the resulting solid material.

Figure 3A:
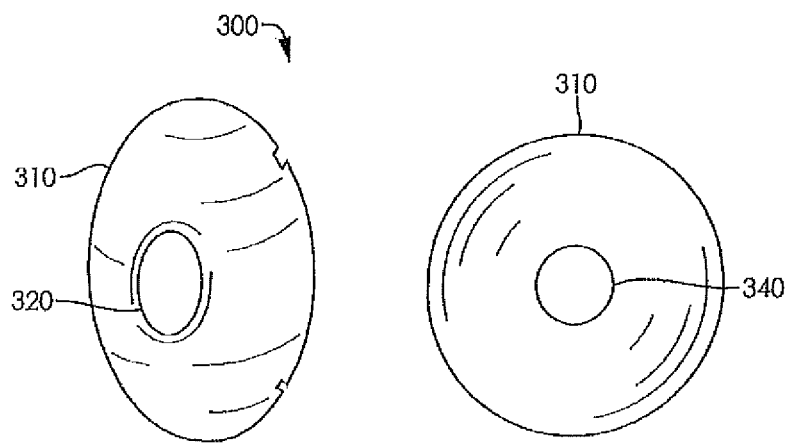
FIG. 3A depicts a third embodiment of a solid material and a mount of a solid state fragrancing object.
Figure 3B:
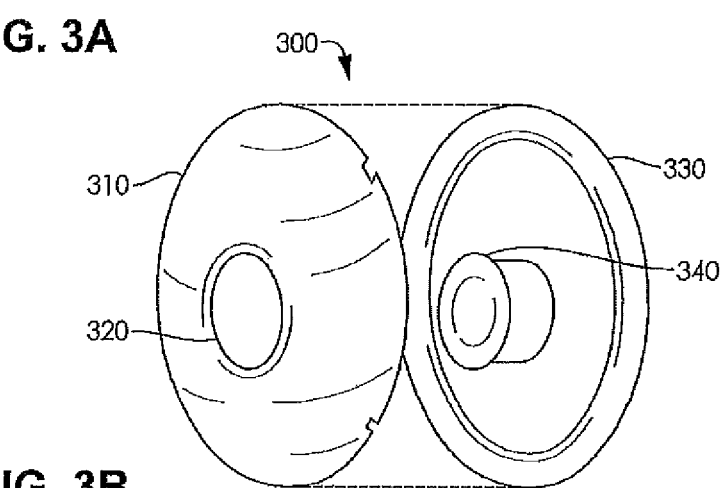
FIG. 3B shows the solid material of FIG. 3A positioned to engage the mount.
Figure 3C:
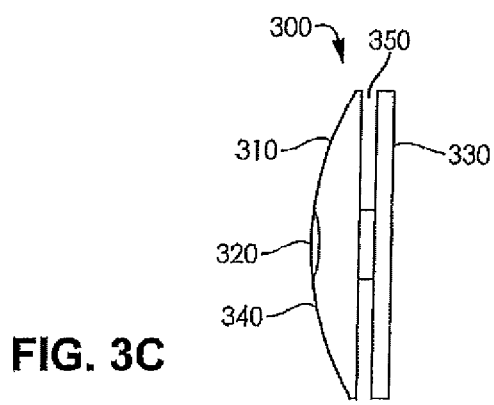
FIG. 3C shows the solid material of FIG. 3A coupled to the mount.

With reference now to FIGS. 3A-3C, a third embodiment of a solid state fragrancing object 300 is shown. The fragrancing object 300 includes a solid material 310 that contains the fragrancing component and an aperture 320 configured to couple to a mount 330. A surface area to volume ratio of the solid material 310 lies between about 0.5:1 to about 50:1. The solid material 310 depicted is substantially disk-shaped; however, other shapes and dimensions can be used. The mount 330 includes a projection 340 that can be coupled to the aperture 320 of the solid material 310. The projection 340 can be configured to provide an airspace 350 between the solid material 310 and a remainder of the mount 330. In this way, the solid material 310 can also emit the fragrance component from the side facing the mount 330. Like other fragrancing objects described herein, the third embodiment of the fragrancing object 300 can be formed, colored, and/or positioned within an environment for inconspicuous applications. It is understood that protrusions or other surface irregularities can be used to increase the surface area to volume ratio as previously described hereinabove.

With reference to FIGS. 4A-4C, a fourth embodiment of a solid state fragrancing object 400 is shown. The fragrancing object 400 includes a solid material 410 and a dispenser 420, where the solid material 410 includes a fragrancing component. The solid material 410 is slidably disposed within the dispenser 420 and operable to move between an enclosed position (shown in FIG. 4A) and an exposed position (shown in FIG. 4B). The solid material 410 has a surface area to volume ratio from about 0.5:1 to about 50:1. The dispenser 420 can be coupled to a mount 430 that can be affixed to a surface, such as a wall. As shown, the dispenser 420 containing the solid material 410 can be configured as a cartridge that is loaded into the mount 430, where the dispenser 420 holds a plurality of solid materials slidably disposed therein. The individual solid materials 410 can be extended or enclosed as desired.

For example, a new solid material 410 can be extended when the fragrancing component of a previously extended solid material 410 is no longer effective at providing fragrancing control. Likewise, one of the solid materials 410 can include a fragrancing component that is different from another of the solid materials 410. This can allow the fragrancing provided by the fragrancing object 400 to be changed or customized as desired. The solid material 410 in FIGS. 4A-4C is depicted as a screen, in particular, a honeycomb screen. The screen shape can optimize airflow through the solid material 410 in order to release the fragrancing component. However, other shapes and forms of the solid material 410 can be employed. The various solid materials 410 in the plurality of solid materials 410 can be individually wrapped or sealed when enclosed by the dispenser 420. In this way, the fragrancing component of the solid material(s) 410 not in use can be preserved. As examples, the solid materials 410 can be exposed by peeling off an adhesive strip or wrapper, and/or the dispenser 420 may have a gasket or seal that protects the solid material 410 from exposure to the environment when enclosed.

With reference to FIGS. 5A-5D, a fifth embodiment of a solid state fragrancing object 500 is shown. The fragrancing object 500 includes a solid material 510 and an enclosure 520. As shown, the enclosure 520 comprises two pieces, a transparent or translucent face plate 530 and an opaque back 540. The solid material 510 includes a fragrancing component and the enclosure 520 encloses the solid material 510. The enclosure 520 includes an aperture 550 configured to expose a portion of the solid material 510. The solid material 510 has a surface area to volume ratio from about 0.5:1 to about 50:1. The solid material 510 can be configured to move within the enclosure 520 to change the portion of the solid material exposed in the aperture 550. For example, as shown in FIGS. 5A-5D, the solid material 510 can be coupled to a projection 560 on the back 540 of the enclosure 520 so that the solid material 510 can be rotated to change the portion of the solid material 510 within the aperture 550. The projection 560 may be coupled to a motor 570 operable to change the portion of the solid material 510 that is exposed in the aperture 550. The motor 570, for example, can rotate the solid material 510 at a rate tailored to provide a continued release of the fragrancing component from the solid material 510 by continuously or periodically changing the portion of the solid material 510 in the aperture 550. Furthermore, a fan 580 can be included that is operable to move air across the portion of the solid material 510 that is exposed in the aperture 550, thereby facilitating release of the fragrancing component from the solid material 510. The fan 580 can be continuously operated, timed to operate at desired intervals, or linked to an actuator, such as a motion sensor or light switch. Operation of the motor 570 and the fan 580 can also be coordinated.

As shown, the solid material 510 is in the form of a disk, but other shapes and configurations are possible. The disk-shaped solid material 510 can be marked with an indicator 590 to identify when replacement is necessary. For example, the indicator 590 can mark when the disk-shaped solid material 510 has rotated a certain distance about the projection 560. In some instances, the indicator 590 can include a stop that physically prevents the disk-shaped solid material 510 from further rotation. For example, the indicator 590 stop can interact with the enclosure 520. The disk-shaped solid material 510 can be in the form of a screen having a honeycomb structure to allow air to circulate through the disk, as depicted in FIGS. 5A-5D.

Figure 6:
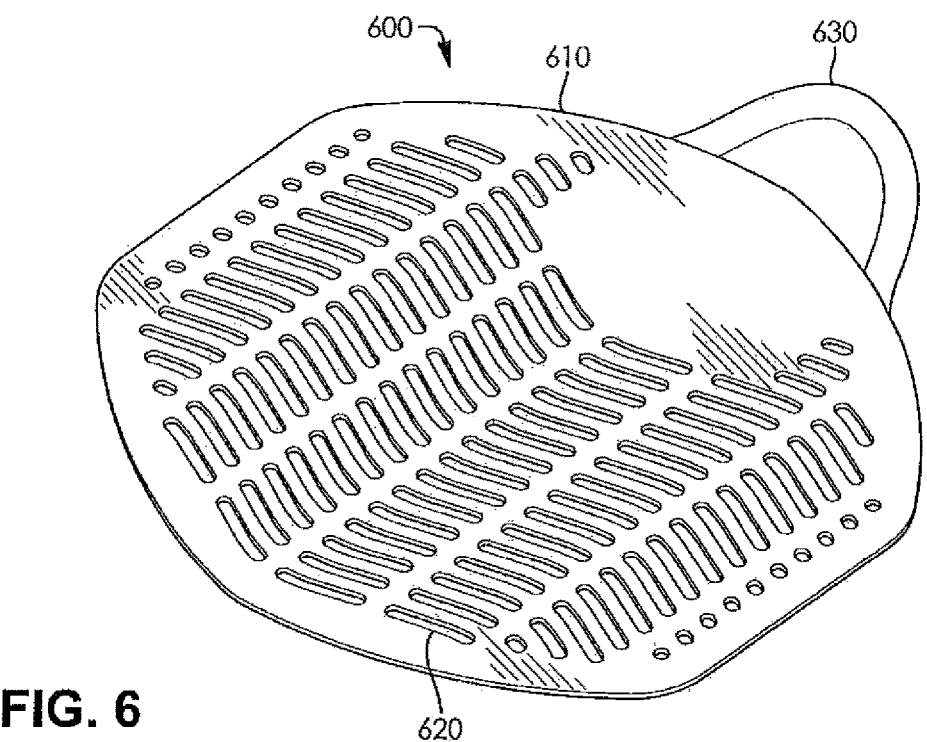
FIG. 6 depicts a sixth embodiment of a solid state fragrancing object.

With reference now to FIG. 6, a sixth embodiment of a solid state fragrancing object 600 is shown. The fragrancing object 600 is configured as a urinal screen 610 that is sized and shaped to cover at least a portion of a urinal drain. The urinal screen 610 is formed of a solid material having a fragrancing component using the various solid materials and fragrancing components as described herein. The urinal screen 610 includes a plurality of apertures 620, where the apertures 620 can vary in size, shape, and frequency across the urinal screen 610. A pick-up loop 630 can be formed therein or added to the urinal screen 610 to facilitate installation and removal of the screen 610. As described herein, the urinal screen 610 comprising the solid material and fragrancing component can be formed by extruding a material and a fragrancing component to form an extruded sheet of solid material. The extruded sheet of solid material can then be die cut or stamped to form the plurality of apertures 620.

The various fragrancing objects described herein can be formed in various colors and can be multicolored. In certain cases, solid colors or translucent colors can be used. Different colors used in combination with different mounting options and different holders or mounts as described herein allow mixing and matching of various colors and provide for an easy change from a less conspicuous stealth display of fragrancing objects to a more conspicuous and brighter display or vice versa. Likewise, design themes and scents of fragrancing components within an environment can be readily replenished or changed altogether. The various fragrancing objects described herein can also incorporate DeoEssence™ olfactory disruption technology by Arylessence, Inc. (Marietta, Ga.).

The present technology provides several advantages and benefits. The solid state fragrancing objects can be easily deployed within an environment by using mounts or holders or by directly coupling the objects to various fixtures or features within the environment. There are no aerosols or liquids used, minimizing environmental impact and any spills or drips. For example, there is no possibility for leaky oil based wick systems to spill and no aerosol fall out on floors creating a sticky or slippery safety hazard. Likewise, there are no special storage or shipping requirements necessary with the present solid state fragrancing objects. The fragrancing objects can be mounted easily in hidden and out of the way locations to reduce theft and vandalism. Fragrance zones created by deploying a system for fragrance control can enhance the experience in the environment and reinforce a general perception of cleanliness. The system can also be mounted in various locations to optimize odor control efficacy and can be customized for environments ranging from small spaces to large spaces. Likewise, the fragrancing component can be tailored to fragrance type and strength preferences; e.g., men's fragrances, women's fragrances, lavatory environment, office environment, commercial or residential environment.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of inconspicuously providing fragrance to a user in an environment comprising:
   disposing a solid state fragrancing object in the environment, the solid state fragrancing object configured as at least a portion of a fixture within the environment, and the solid state fragrancing object comprising a solid material mixed with a fragrancing component;
   wherein the solid state fragrancing object covers a preexisting portion of the fixture or replaces a portion of the fixture.

2. The method of claim 1, wherein the solid state fragrancing object is configured as at least a portion of a trim piece of the fixture.

3. The method of claim 1, wherein the fixture includes a container or a receptacle and the solid state fragrancing object is disposed within the lid of the container or the receptacle.

4. The method of claim 1, wherein the fixture includes a sink or a countertop and the solid state fragrancing object is disposed under the sink or the counter top.

5. The method of claim 1, wherein the fixture includes plumbing and the solid state fragrancing object conforms to the shape of the plumbing.

6. The method of claim 1, wherein the fixture includes part of a heating, ventilation, and air conditioning (HVAC) system and the solid state fragrancing object is disposed on part of the HVAC system.

7. The method of claim 1, wherein the fixture comprises a member selected from the group consisting of a lavatory stall door, a lavatory stall wall, a lavatory stall upright, and a urinal divider.

8. The method of claim 1, wherein the fixture comprises a member selected from the group consisting of a hand dryer, a paper towel dispenser, a soap dispenser, and a waste receptacle.

9. The method of claim 1, wherein the fixture comprises a member selected from the group consisting of a shelf and an entry or exit door to the environment.

10. The method of claim 1, wherein the fixture comprises an air vent.

11. The method of claim 1, wherein the fixture comprises a light fixture.

12. The method of claim 1, wherein the solid state fragrancing object is disposed within a line of sight of the user.

13. The method of claim 1, wherein the solid state fragrancing object is disposed out of the line of sight of the user.

14. The method of claim 1, wherein the solid state fragrancing object provides a square inch of fragranced surface area to environmental cubic foot volume ratio of about 0.01 to about 0.1.

15. The method of claim 1, wherein the solid material has a substantially constant cross-sectional area in a longitudinal dimension and a surface area to volume ratio from about 0.5:1 to about 50:1.

16. The method of claim 1, wherein disposing a solid state fragrancing object in the environment comprises disposing a plurality of the solid state fragrancing objects in the environment.

17. The method of claim 16, wherein the solid state fragrancing objects are disposed on more than one fixture.

18. The method of claim 17, wherein the solid state fragrancing objects disposed on different fixtures comprise different fragrancing components.

19. The method of claim 1, wherein the solid state fragrancing object substantially matches a color of the fixture.

20. The method of claim 1, wherein the solid state fragrancing object substantially matches a texture of the fixture.

21. The method of claim 1, wherein the solid state fragrancing object is removably coupled to the fixture.

22. The method of claim 21, wherein the solid state fragrancing object is removably coupled to the fixture by one of a mount and a base.

23. The method of claim 21, wherein the solid state fragrancing object is directly coupled to the fixture.

24. The method of claim 1, wherein the solid material includes one of a thermoplastic elastomer and a polyolefin elastomer.

25. The method of claim 24, wherein the solid material includes the thermoplastic elastomer and the thermoplastic elastomer includes a polyether block amide.

26. The method of claim 1, wherein the fragrancing component comprises a fragrance oil.

* * * * *